(12) United States Patent
Brisson et al.

(10) Patent No.: US 8,173,414 B2
(45) Date of Patent: May 8, 2012

(54) SULFIDE PERFUSION APPARATUS

(76) Inventors: Jerome E Brisson, Chaplin, CT (US);
David Kraus, Birmingham, AL (US)

( * ) Notice: Subject to any disclaimer, the term of this patent is extended or adjusted under 35 U.S.C. 154(b) by 1096 days.

(21) Appl. No.: 12/027,741

(22) Filed: Feb. 7, 2008

(65) Prior Publication Data

US 2008/0193911 A1 Aug. 14, 2008

Related U.S. Application Data

(60) Provisional application No. 60/900,255, filed on Feb. 8, 2007.

(51) Int. Cl.
*A01N 1/00* (2006.01)
*A01N 1/02* (2006.01)
(52) U.S. Cl. ..................................... 435/284.1; 435/1.2
(58) Field of Classification Search .................. None
See application file for complete search history.

(56) References Cited

FOREIGN PATENT DOCUMENTS
WO WO 00/18226 * 4/2000

OTHER PUBLICATIONS

Johansen et al., "Exogenous hydrogen sulfide protect against regional myocardial ischemia-reperfusion injury", Basic Research in Cardiology 101 : 53-60 (2006).*
Salimi et al., "Renewable-surface sol-gel derived carbon ceramic electrod fabricated by [Ru(bpy)(tpy)CI]PF6 and its application as an amperometric sensor for sulfide and sulfur oxoanions", Analyst 127 : 1649-1656 (2002).*

* cited by examiner

*Primary Examiner* — Sandra Saucier
(74) *Attorney, Agent, or Firm* — Tomas Friend

(57) ABSTRACT

An apparatus for establishing sulfide perfusion is described and includes a sulfide supply for introducing sulfide into fluid for perfusion, an apparatus for delivery of the perfusion fluid, a fluid chemistry monitor for monitoring the concentration of sulfide and other components of the perfusion fluid, and an electronic controller connected with the sulfide supply and the fluid chemistry monitor to control the sulfide supply to regulate the sulfide concentration of the perfusion fluid based on input from the fluid chemistry monitor.

15 Claims, 4 Drawing Sheets

SULFIDE PERFUSION APPARATUS

CROSS-REFERENCE TO RELATED APPLICATIONS

This application claims priority to provisional application 60/900,255 filed Feb. 8, 2007 and application Ser. No. 11/652,836 filed Jan. 12, 2007.

STATEMENT REGARDING FEDERALLY SPONSORED RESEARCH OR DEVELOPMENT

Not Applicable

INCORPORATED-BY-REFERENCE OF MATERIAL ON A CD

Not Applicable

BACKGROUND OF THE INVENTION

1. Field of the Invention

This invention relates to the establishment and maintenance of Fluid Sulfide Perfusion for therapeutic, scientific and medical purposes.

2. Description of Related Art

Sulfide is now known to play important roles in mammalian cell signaling. These include regulation of vascular smooth muscle tone, neuronal activity, liver bile production and general cell protection from the oxidative stress of aerobic metabolism. Because of the potential toxicity of hydrogen sulfide ($H_2S$), its cellular/organismal concentration is tightly regulated by enzymatic production and consumption pathways so that toxic levels are not reached. However, too little sulfide, equivalent to too little reducing power and consequently too much oxidative stress, has been linked to cellular apotosis.

One way in which sulfide may achieve beneficial effects is by acting as a global cellular and organismal reductant, capable of shifting the cellular reductive/oxidative (redox) balance towards the reduced state and protecting against oxidative damage. Most cellular reductants are larger molecules compared to $H_2S$ and sulfide, and therefore cannot diffuse as rapidly, readily pass through cell membranes, or fit into smaller molecular spaces where some oxidized thiols occur. Therefore sulfide may be one of the most important cellular defenses against oxidative stress.

$H_2S$ and other sulfide compounds are regularly produced by human cellular metabolism. Sulfide levels can be augmented by the introduction of $H_2S$ rich gas, fluid or various sulfide supply compounds.

A variety of materials, both naturally occurring and artificially manufactured may be available for use as sulfide supply compounds. Sulfide supply compounds are chosen for their compatibility with each specific application. Diallyl Disulfide from Garlic or Lenthionine from Shitake mushrooms are derived from edible plants and are therefore likely to be safe. Flavor compounds presently used in food processing may also be used as sulfide supply compounds. Such compounds include but are not limited to Trithioacetone, 2-Thiophenethiol, and Dimethyl Trisulfide.

The short and long term repair and preservation of living biological material such as cultured cells, stem cells, bone, and whole organs is essential for the use of this material in research and clinical applications such as tissue growth and transplantation. Repair and preservation materials and methods are designed to limit oxidative damage and loss of viability. Although sulfide is produced endogenously, serving to protect cellular redox balance, compromised redox regulatory pathways in isolated cells or organs can be augmented by the exogenous addition of sulfide. A sulfide supply system designed to expose biological material to specific sulfide supply compounds, the ability to maintain concentration and rate of delivery during repair and preservation procedures could be used to enhance the viability of preserved samples, repair damaged tissue and enhance growth procedures.

BRIEF DESCRIPTION OF THE INVENTION

In one aspect, the present invention is an apparatus for establishing sulfide perfusion.

In another aspect, the present invention is a method for perfusing a receiver with sulfide perfusion fluid.

In yet another aspect, the present invention is a method for preserving the viability of an organ by perfusing it with a sulfide rich perfusion fluid.

In yet another aspect, the present invention is a sulfide supply means, which may incorporate any means of sulfide supply, including the sulfide supply means in U.S. patent application Ser. No. 11/652,836 entitled "SULFIDE BATH", filed Jan. 12, 2007.

The sulfide supply according to the present invention provides for the perfusion of sulfide rich fluid to be used, for example, as a preservation agent, an antioxidant, or a metabolic regulator. The sulfide rich fluid may comprise other useful components such as chemicals, drugs, and nutrients and may flow into, through, over, and/or around a receiver. A sulfide supply may be delivered to a receiver such as a living or non-living body, portion of a body, organ, tissue, cell, or device. A sulfide supply may be delivered to a receiver device in fluid communication with biological material such as a living or non-living body or portion of a body. Delivery of fluid to a receiver may be accomplished using any suitable delivery means including pumping, gravity flow, and suctioning.

A sulfide perfusion system may include a fluid chemistry monitoring means comprising a sulfide sensing system designed to operate with the sulfide perfusion system and/or to interface with other medical or research equipment. The temperature, pH, concentration, flow rate, and pressure of sulfide solution may be sensed and regulated. Effluent from the perfusion system may be monitored, stored, recirculated, and/or discarded and remain in the receiver or be removed. The sulfide sensing system may monitor any airspace, within or outside of the preparation or apparatus to control gaseous hydrogen sulfide and may include sensing of an organ tissue, cell, or other preparation to provide feedback to the fluid chemistry monitoring system. A sulfide sensing system may also measure a biological response that serves as a sensing system to provide feedback to the fluid chemistry monitoring system.

A sulfide perfusion system may comprise automatic and/or manual controls. The controls for a sulfide perfusion system may be local and/or remote and may be of an electric, pneumatic, hydraulic, wireless or other type. The sulfide perfusion system may comprise a local and/or remote display showing data from a sulfide sensing system.

DETAILED DESCRIPTION OF THE INVENTION

Figure 1:
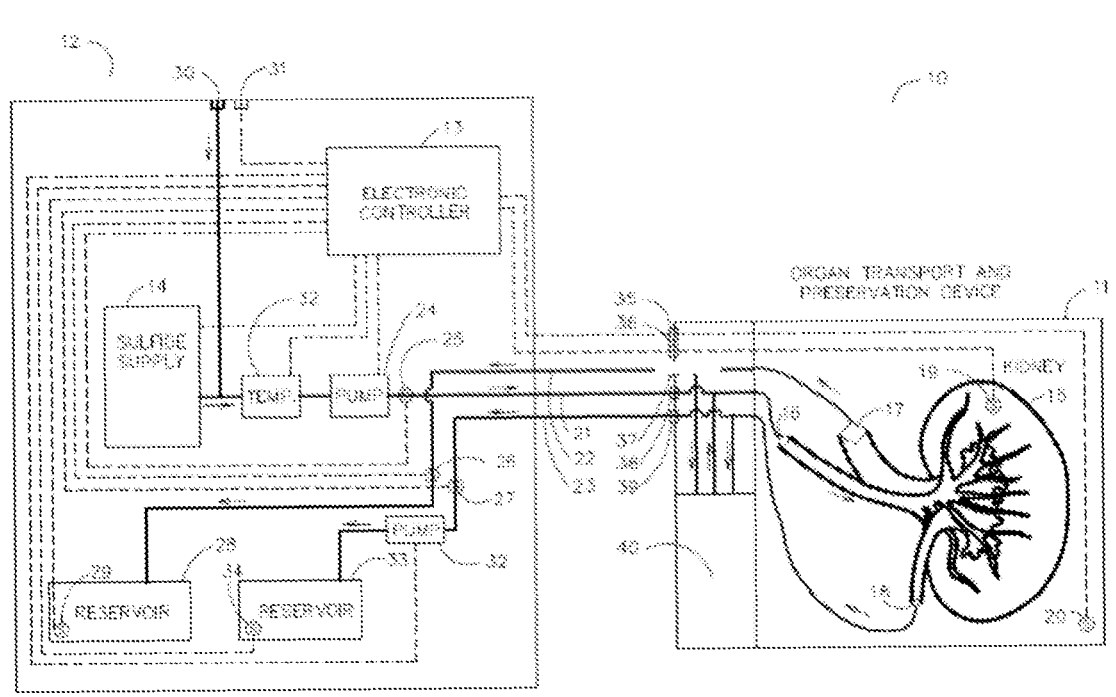
FIG. 1 is a schematic view of an apparatus for establishing sulfide perfusion, according to an embodiment of the present invention. Sulfide perfusion of an isolated organ is established through the arterial and venous vascular segments such as illustrated with a kidney, however similar perfusions may be established with various organs or biological preparations.

The term "sulfide" as used herein is not necessarily limited to the particular species $H_2S$, but includes the sulfide species $H_2S$, $HS^-$, $S^{-2}$, and sulfide donor molecules, unless otherwise specified. A sulfide source or sulfide supply may comprise sulfide donating molecules dissolved into solution that can be used to add sulfide such as Diallyl Disulfide, Lenthionine, Trithioacetone, 2-Thiophenethiol, and Dimethyl Trisulfide. In such cases sulfide is delivered to a receiver as a sulfide donor, which releases sulfide in the receiver and the feedback regulation system adjusts the delivery of the fluid stock of sulfide donating molecules to maintain a desired sulfide concentration. The present invention is not limited to establishing a particular sulfide concentration. The sulfide concentration should be optimized for the particular application of the receiver device to which the sulfide perfusion apparatus will be connected. Total sulfide concentration is the sum total of sulfide species concentrations of $H_2S$, $HS^-$, $S^-$, and their sulfide donor equivalents in a solution.

The term "electronic controller" can include dedicated electronic control devices, such as a proportional integral derivative (PID) controller, or multi-purpose devices such as a personal computer. Additionally, "electronic controller" does not necessarily specify a unitary device. For instance, a laptop computer used in connection with a separate input/output device qualifies as an "electronic controller." Also, "electronic controller" does not necessarily specify a single control unit. For example, an apparatus in which one control unit controlled the sulfide supply means, another control unit separately controlled the airspace $H_2S$ mitigation and warning means, and a further control unit was used to control the sulfide perfusion arrangement would still fall within the meaning of the term "electronic controller."

The term "sensor" as is used herein is generic to all types of sensing devices, and is not necessarily limited to sensors providing substantially continuous and/or proportional outputs. While sensors described herein are generally capable of providing substantially continuous proportional inputs to the electronic controller, other types of sensors can also be employed in connection with the present invention. For instance, a switch, such as a pressure switch, level switch, or temperature switch, providing output signals only at discrete set points, can be used in place of a pressure sensor with a continuous, proportional output. Generally, the particular type of sensor is chosen based on the demands of the particular application and cost considerations.

Control of various components by an electronic controller is not limited to a particular control scheme or logic. For instance, the control of sulfide addition by the electronic controller can be a simple ON/OFF control, where a constant addition is directed until a desired sulfide concentration is reached, or the control can be a variable, proportional control, where a variable addition rate is adjusted based on continuous sensor feedback to maintain the sulfide concentration within a given range.

A "connection" between an electronic controller and sensors and other components is not limited to a particular type of connection. For instance, a connection may be a direct electrical connection, optical connection, wireless connection, indirect connection through relays or other intermediate components.

Referring to FIG. 1, an apparatus 10 for establishing sulfide perfusion comprises a sulfide perfusate supply 12 for providing a precisely controlled sulfide rich fluids, a sulfide supply 14 for introducing sulfide into the fluid, and an electronic controller 13 for monitoring input from sensors and for controlling equipment connected to a medical device 11 through fluid conduits, wiring for fluid chemistry monitoring, and/or other attachments required for a complete system. A medical device 11 for containment of a receiver 15, which in this embodiment is a kidney or other organ, comprises sensors 19 and 20 to monitor the state of the receiver the environment inside medical device 11 and mechanical apparatus 40.

Figure 2:
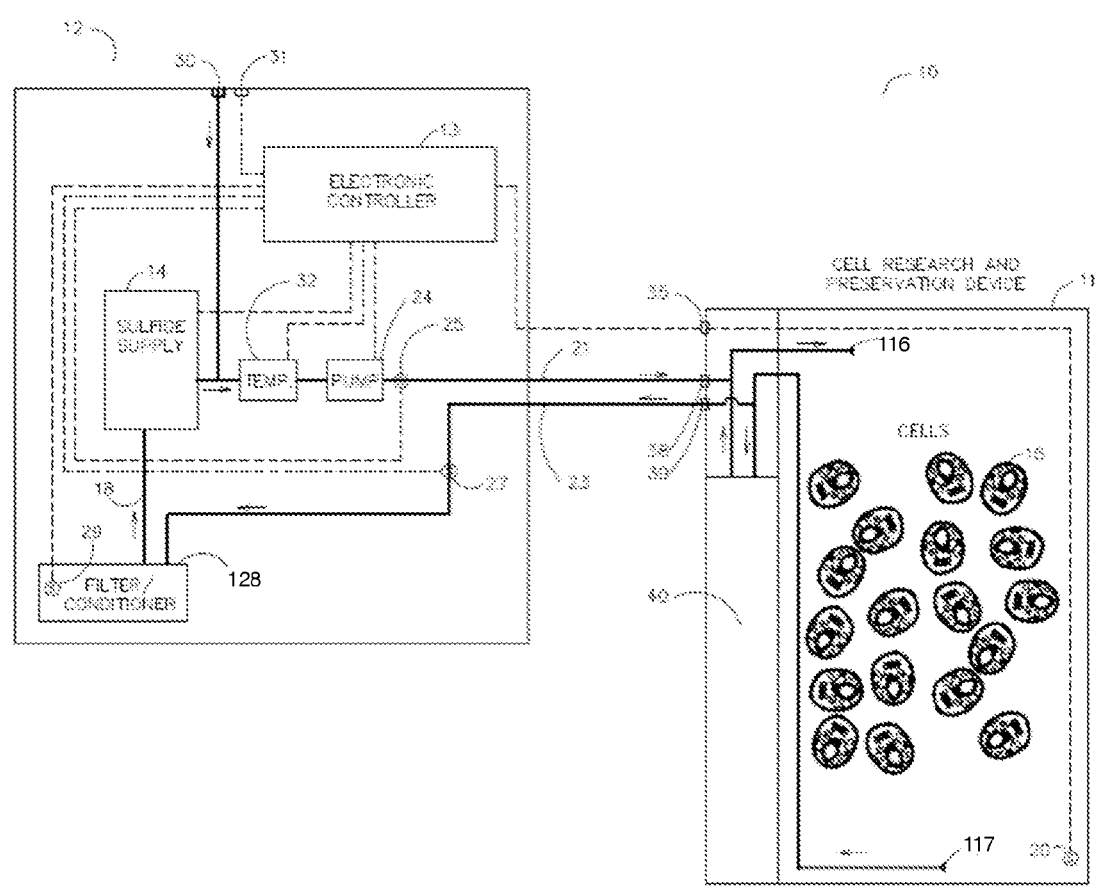
FIG. 2 is a schematic view of an apparatus for establishing sulfide superfusion, according to an embodiment of the present invention. Sulfide superfusion is established by bathing cells or tissues in a stream of flowing perfusion fluid, however similar perfusions may be established with various biological preparations.

Mechanical apparatus 40 delivers perfusion fluid into a renal artery of the organ through fluid connection 16 and incorporates a fluid conduit to attachment 38 to introduce sulfide rich fluids for sulfide rich perfusion of receiver 15. Mechanical apparatus 40 removes venous effluent from the organ through fluid attachment 17, which provides a fluid connection from a renal vein of the organ to mechanical apparatus 40 via conduit 22 for effluent removal, and may incorporate a fluid conduit to attachment 37 for use in sulfide perfusion system. Mechanical apparatus 40 removes effluent fluid from the ureter of the kidney through fluid attachment 18, which provides a fluid connection from the ureter to mechanical apparatus 40 via conduit 23, and may incorporate attachment 39 for use in the sulfide perfusion system. Effluent in conduit 22 is monitored by sensor 26 prior to effluent delivery into reservoir 28. Effluent in conduit 23 is monitored by sensor 27 prior to effluent delivery into reservoir 33. A pump 32 may be installed in conduit 23 to provide controlled suction for removal of effluent from ureter. Sensors 29 and 34 monitor the effluents held in reservoirs 28 and 33. One or more of reservoirs 28 and 33 may be replaced by a filter/conditioner in a recirculation loop 128 as shown in FIG. 2, in embodiments requiring such conditions. Depending on the nature of the medical device 11 and the biological preparation 15 effluent may be retained by medical device 11 eliminating the need for attachment 37, attachment 39, conduit 22, conduit 23 and the associated reservoir or filter and recirculation apparatus within sulfide perfuse supply 12. Pump 24, with pressure regulation, when turned on by electronic controller 13, pumps fluid from sulfide supply 14 through a temperature regulator 32, to establish a desired temperature for the sulfide supply, and through conduit 21 to deliver fluid for sulfide perfusion to medical device 11 at attachment 38 for perfusion of receiver 15. Sensor 25 is located in conduit 21 to monitor perfusion fluid. Electronic controller 13 controls sulfide supply 14, temperature regulator 32, and pump 24. Additional pumps, temperature regulators, fluid conduits, sensors, and other components may be used for more complex organs, such as a heart or liver, to facilitate precise control over perfusion of different regions or lobes of the organ or the environment surrounding the organ. Sulfide sensing systems include sensors located in medical device 11 to provide feedback to electronic controller 13 and adjust the sulfide perfusate supply. Sensor 19 is connected to attachment 36 by wire or other control mechanism which is connected to the electronic controller 13. Sensor 20 is connected to attachment 35 by wire or other control mechanism and then connected to the electronic controller 13. Port 30 may be used to add nutrients or other compounds to the sulfide perfusate in conduit 21. Port 31 may be used for electronic input and output devices and may be used for communication with medical device 11.

Referring to FIG. 2, an apparatus 10 for establishing sulfide perfusion comprises a sulfide perfusate supply 12 for providing precisely controlled sulfide rich fluids, a sulfide supply 14 for introducing sulfide or sulfide donor into the fluid, and an electronic controller 13 for monitoring input from sensors and for controlling equipment that is connected to a medical device 11 through fluid conduits, wiring for fluid chemistry monitoring and other attachments necessary for a complete system. A medical device 11 for containment of a receiver 15, which in this embodiment comprises cells, comprises a sensor 20 to monitor the environment inside the vessel. Medical device 11 comprises a mechanical apparatus 40, sulfide perfusate dispenser 116, and fluid conduit from mechanical apparatus 40 to sulfide perfusate dispenser 116, which connects to sulfide supply conduit 21 through attachment 38 and provides sulfide perfusion to the cells. Medical device 11 also comprises a fluid conduit from mechanical apparatus 40 to an effluent inlet 117, which may incorporate a fluid conduit to attachment 39 for removal of effluent for use in sulfide perfusion system. Effluent in conduit 23 is monitored by sensor 27 prior to entering into filter/conditioner 128, which connects to sulfide supply 14 by attachment 18, providing a re-circulation loop. A sensor 29 monitors the effluent in filter/conditioner 128. Either a filter/conditioner 128 with a re-circulation loop or a reservoir 28 as shown in FIG. 1 may be used, as conditions require. Depending on the nature of the medical device 11 and the cell/cells 15, effluent may be retained by medical device 11 eliminating the need for attachment 39, conduit 23 and the associated reservoir or filter and recirculation apparatus within sulfide perfuse supply 12. Pressure regulated pump 24, when turned on by electronic controller 13, pumps fluid from sulfide supply 14, which is at a desired temperature after passing through temperature regulator 32, and continues through conduit 21 to provide fluid for sulfide perfusion of receiver 15. Electronic controller 13 controls sulfide supply 14, temperature regulator 32, and pump 24. Additional pumps, temperature regulators, fluid conduits, sensors, and/or other components may be required for more complex cell research and preservation devices, such as stem cell devices or blood preservation devices, allowing precise control of perfusion. Port 30 may be used to add nutrients or other compounds to sulfide perfusate in conduit 21. A sulfide sensing system may include sensors located in medical device 11 to provide feedback to electronic controller 13 and adjust the sulfide perfuse supply. Sensor 20 is connected to attachment 35 by wire or other control mechanism, which is connected to the electronic controller 13. Port 31 may be used for connection to electronic input and output devices.

Figure 3:
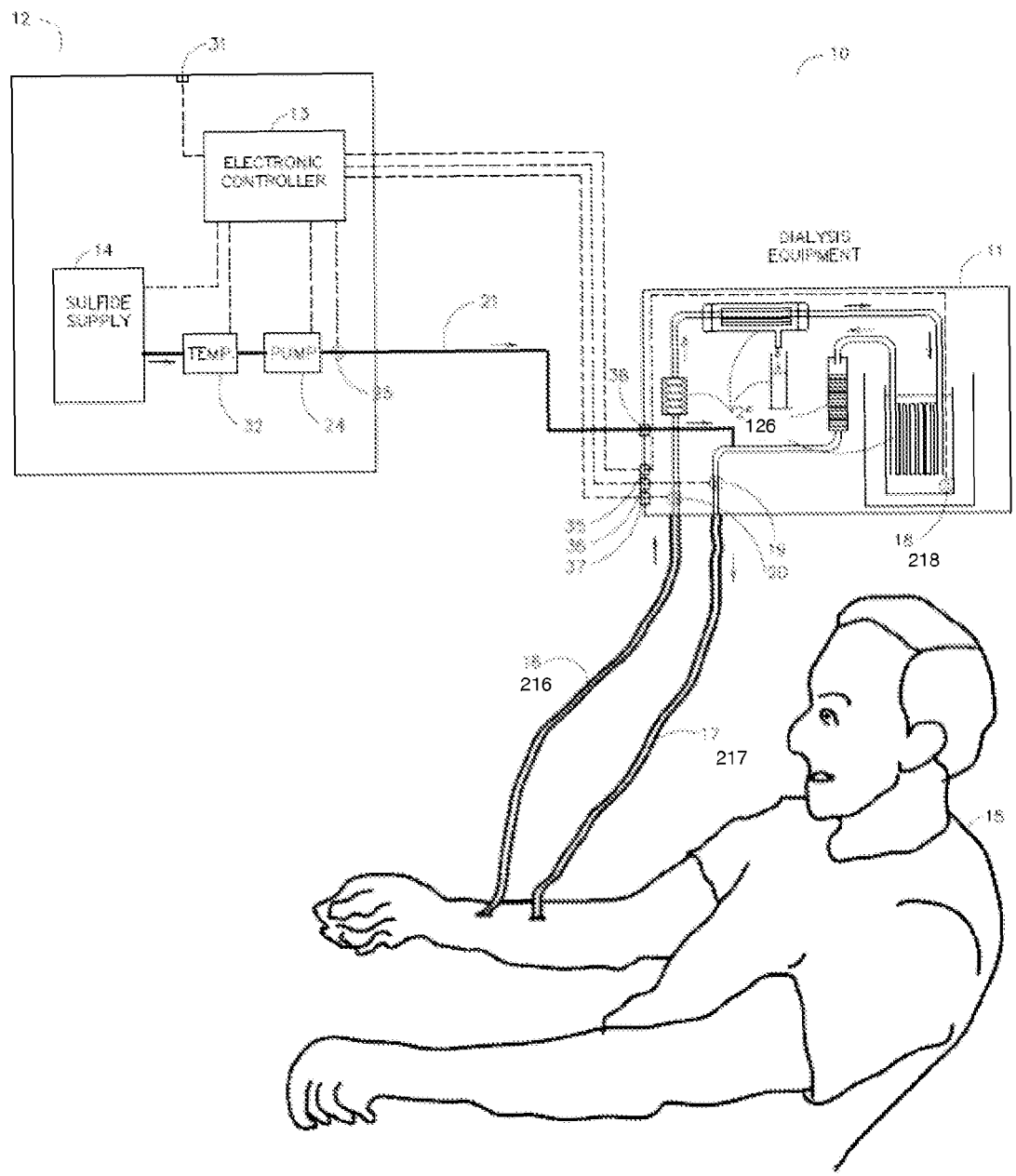
FIG. 3 is a schematic view of an apparatus for establishing sulfide perfusion, according to an embodiment of the present invention. Sulfide perfusion is established by introducing perfusion fluid to dialysis equipment, which subsequently delivers the perfusion fluid into a body, however similar perfusions may be established with various equipment and various biological preparations.

Referring to FIG. 3, an apparatus 10 for establishing sulfide perfusion comprises a sulfide perfusate supply 12 for providing precisely controlled sulfide rich fluids, a sulfide supply 14 for introducing sulfide into the fluid, and an electronic controller 13 for monitoring input from sensors and for controlling equipment which, is connected to a medical device 11 through fluid conduits, wiring for fluid chemistry monitoring and other attachments necessary for a complete system. Medical equipment 11, which in this embodiment is a dialysis machine, comprises internal equipment 126, for treatment of a receiver 15, which is a human patient in this embodiment. Internal equipment 126 may comprise a sensor 19 to monitor the fluid outlet, which enters hose 217 of the dialysis machine. A fluid conduit connects internal piping attached to hose 217 with attachment 38 to allow for introduction of sulfide rich perfusate to the patient. Internal equipment 126 may comprise a sensor 20 to monitor fluid coming from receiver 15, through hose 216. A sensor 218 may be located to monitor the state of fluid within internal equipment 126. Pump 24, when turned on by electronic controller 13, pumps fluid from sulfide supply 14, which is at a desired temperature after passing through temperature regulator 32, continues through conduit 21, connecting to attachment 38 and outlet piping of medical equipment 11 to provide fluid for sulfide perfusion of receiver 15. Sensor 25 is located in conduit 21 to monitor perfusion fluid. Electronic controller 13 controls sulfide supply 14, temperature regulator 32, and pump 24. A sulfide sensing system comprises sensors located in medical device 11 which provide feedback to electronic controller 13 and adjust the sulfide perfusate supply. Sensor 218 is connected to attachment 35 by wire or other control mechanism, which is connected to the electronic controller 13. Sensor 19 is connected to attachment 36 by wire or other control mechanism, which is connected to the electronic controller 13. Sensor 20 is connected to attachment 37 by wire or other control mechanism, which is connected to the electronic controller 13. Port 31 is available for electronic input and output devices and may be used for communication with medical device 11.

Figure 4:
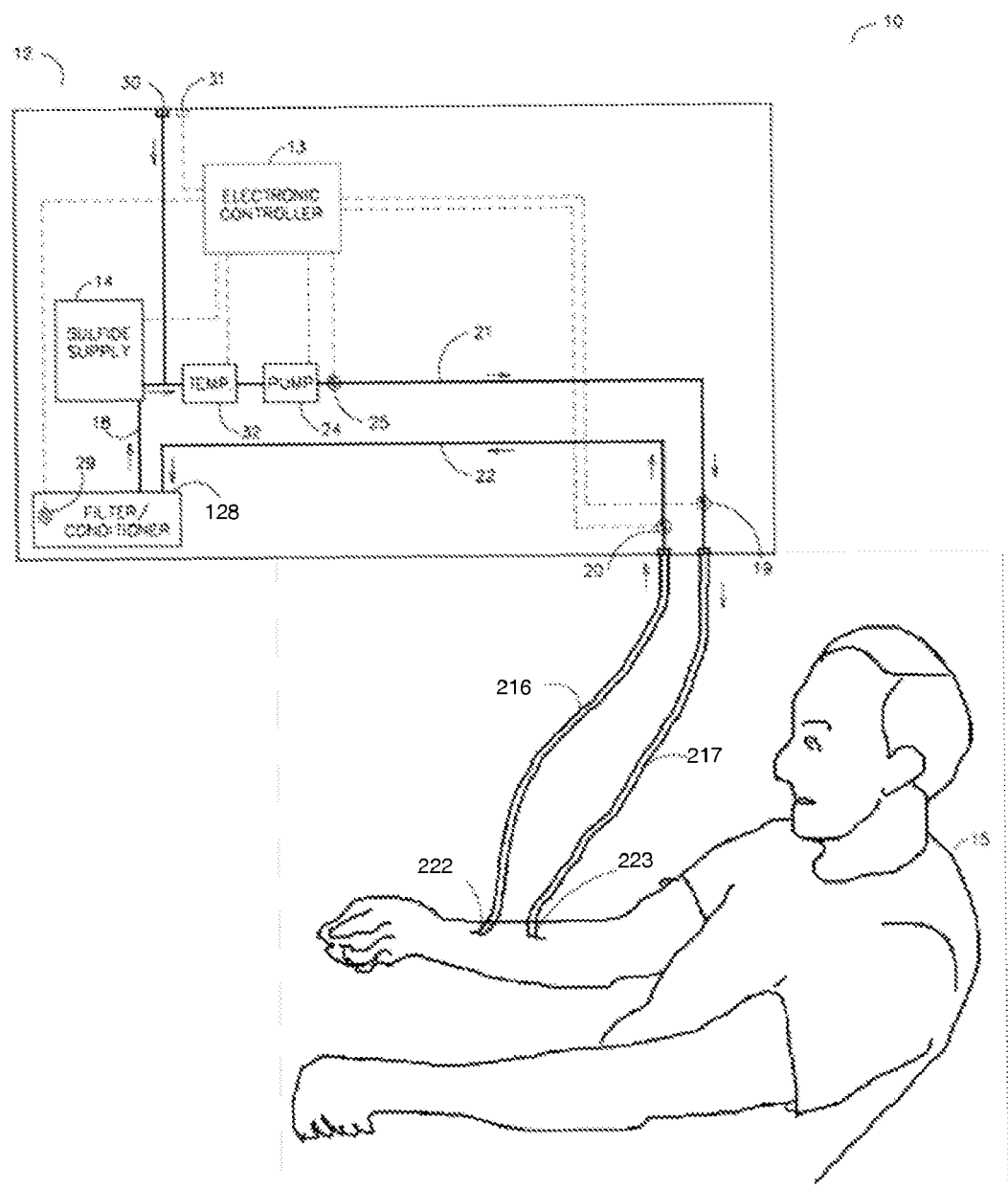
FIG. 4 is a schematic view of an apparatus for establishing sulfide perfusion, according to an embodiment of the present invention. Sulfide perfusion is established by introducing perfusion fluid directly into a body, however similar perfusions may be established to perfuse an entire body, a portion of a body or multiple perfusions, each with specific fluid content.

Referring to FIG. 4, an apparatus 10 for establishing sulfide perfusion includes a sulfide perfusate supply 12 for providing precisely controlled sulfide rich fluids, a sulfide supply 14 for introducing sulfide into the fluid, and an electronic controller 13 for monitoring input from sensors and for controlling equipment. Sulfide body perfusion, shown as, but not limited to, the entire body, may be modified to perfuse certain portions of the body. Sulfide body perfusion may also be used in a deceased body for the purpose of organ and tissue preservation prior to removal from the body, providing enhanced viability of specimens for transplantation and other medical uses. Sulfide supply conduit 21 may have a sensor 19 to monitor the fluid outlet, which enters hose 217, then enters receiver body 15 through blood artery 223. Effluent conduit 22 may have a sensor 20 to monitor fluid coming from receiver body 15, through blood vein 222 and hose 216. Effluent in conduit 22 enters into filter/conditioner 128 which connects to sulfide supply 14 by conduit 18, forming a re-circulation loop. A sensor 29 monitors the effluent in filter/conditioner 128. Either filter/conditioner with re-circulation loop, or reservoir as shown in FIG. 1 may be used, as conditions require. Pressure regulated pump 24, when turned on by electronic controller 13, obtains fluid from sulfide supply 14, which is at the proper temperature after passing through temperature regulator 32, and continues through conduit 21, connecting to hose 217 to provide fluid for sulfide perfusion of receiver 15. Sensor 25 is located in conduit 21 to monitor perfusion fluid. Electronic controller 13 controls sulfide supply 14, temperature regulator 32 and pump 24. Additional pumps, temperature regulators, fluid conduits, sensors, and other components may be used to facilitate precise control over perfusion of different regions or organs of the body or the environment surrounding them. Sulfide sensing systems include sensors located in sulfide perfusate supply 12 and may include sensors to measure a biological response of receiver 15 to provide feedback to electronic controller 13 and adjust the sulfide perfusate supply. Port 30 may be used to add nutrients or other compounds to sulfide perfusate in conduit 21. Port 31 may be used for electronic input and output devices.

The present invention is not limited to the embodiments and aspects shown and described. Instead, various modifications and adaptations to particular circumstances can be made while remaining within the scope of the present invention.

The present invention further includes the use of redundant components to enhance the safety and reliability of operation. For instance, multiple sulfide sensors or measured biological parameters can be employed with a sulfide sensing system to mitigate the impact of sensor failure. In addition to simple redundancy of components, an electronic controller 13 can be further configured to optimize the effectiveness of the redundant components. For example, if multiple sulfide sensors are employed, the electronic controller 13 can more accurately determine sulfide concentration by averaging the sensor inputs. The electronic controller 13 can also be configured to indicate a sensor or sensors as faulty if the inputs fall outside of a given tolerance from other sensors.

The actions directed by electronic controller 13 in response to a high $H_2S$ gas concentration in the airspace surrounding the sulfide perfusion 10 can be taken simultaneously, or incrementally. For example, the electronic controller 13 can direct the ventilation of the airspace upon reaching a first limit, direct the sulfide supply means 14 to stop adding sulfide at a second limit, and activate an alarm unit at a third limit, or one or more of these actions can be taken simultaneously at the same limit. The present invention is also not limited to the particular corrective actions enumerated herein.

As most of the sulfide perfusion systems are enclosed, no airspace $H_2S$ warning and mitigation means is described in connection with the apparatus 10, although warning and/or mitigations means could also be included within the scope of the present invention. Sulfide perfusion system 10 could also be placed in a ventilation hood to vent any gases.

The invention claimed is:

1. An apparatus for establishing sulfide perfusion of a receiver comprising:
    a perfusion fluid supply comprising:
    a sulfide supply configured for introducing sulfide into a perfusion fluid to form a sulfide-containing perfusion fluid,
    a fluid conduit configured for delivering the sulfide-containing perfusion fluid to the receiver,
    a first sulfide sensor configured to measure the sulfide concentration in the sulfide-containing perfusion fluid before said sulfide-containing perfusion fluid reaches the receiver, and
    a controller configured to receive input from the first sulfide sensor and to use said input to control the introduction of sulfide into the perfusion fluid and thereby regulate sulfide concentration in the sulfide-containing perfusion fluid.

2. The apparatus of claim 1 wherein the sulfide supply comprises a solution containing a sulfide donor selected from the group consisting of: Diallyl Disulfide, Trithioacetone, 2-Thiophenethiol, Dimethyl Trisulfide, Lenthionine, and combinations thereof.

3. The apparatus of claim 1, wherein the controller further controls the temperature and the pressure, of the sulfide-containing perfusion fluid and the perfusion supply further comprises:
    a pressure sensor connected to the controller and configured to measure the pressure of the sulfide-containing perfusion fluid delivered to the receiver,
    a temperature sensor connected to the controller and configured to measure the temperature of the sulfide-containing perfusion fluid,
    a pump connected to the controller and configured to pump the sulfide-containing perfusion fluid through the conduit to the receiver, and
    a temperature regulator configured to configured to control the temperature of the sulfide-containing perfusion fluid.

4. The apparatus of claim 1, and further comprising a medical device containing the receiver and a mechanical apparatus that delivers the perfusion fluid to the receiver and wherein fluid from the sulfide supply and perfusion fluid from the mechanical apparatus mix to form said sulfide-containing perfusion fluid.

5. The apparatus of claim 4, wherein the mechanical apparatus collects effluent fluid from the receiver.

6. The apparatus of claim 5, and further comprising one or more sensors configured to measure a state of the perfusion fluid and/or the sufide-containing perfusion fluid, said state being selected from the group consisting of: pH, temperature, pressure, sulfide concentration, osmolarity, nutrient concentration, drug concentration, metabolite concentration, and combinations thereof.

7. The apparatus of claim 4, wherein the receiver is an organ, a part of an organ, a tissue, or a cell culture and further comprising:
    a second sulfide sensor connected to the controller and configured to monitor a sulfide concentration in the receiver,
    a third sulfide sensor connected to the controller and configured to monitor a sulfide concentration inside medical device,
    a pressure regulator controlling the pressure of the perfusion fluid, and
    a temperature regulator establishing a desired temperature for the perfusion fluid.

8. The apparatus of claim 4, wherein
    the mechanical apparatus delivers perfusion fluid into a circulatory vessel in the receiver or around the receiver.

9. The apparatus of claim 1, wherein the receiver is a medical device in fluid communication with a vasculature in a living patient or non-living body and wherein the medical device comprises:
    a mechanical apparatus that delivers sulfide-containing perfusion fluid into the vasculature of the receiver comprising:
    a second sulfide sensor monitoring a sulfide concentration in the receiver,
    a pressure regulator controlling the pressure of the sulfide-containing perfusion fluid delivered to the receiver, and
    a temperature regulator establishing a desired temperature for the sulfide-containing perfusion fluid.

10. The apparatus of claim 9, wherein the receiver is a living patient the medical device is a dialysis machine.

11. The apparatus of claim 1, and further comprising a temperature regulator that heats or cools the sulfide-containing perfusion fluid to a set temperature.

12. The apparatus of claim 6, wherein the receiver is an isolated kidney; the fluid conduit is configured to deliver the sulfide-containing perfusion fluid into a renal artery; effluent is collected from a renal vein and from a ureter; and second and third sulfide sensors are configured to measure sulfide concentrations in the effluents from the renal vein and ureter, respectively.

13. The apparatus of claim 1, and further comprising:
  a first fluid conduit configured to form a fluid connection between the sulfide supply and an artery in a patient,
  a second fluid conduit configured to receive an effluent from a vein in the patient and deliver the effluent to the sulfide supply,
  a sensor configured to measure a state of the effluent, said state being selected from the group consisting of pH, temperature, pressure, sulfide concentration, osmolarity, nutrient concentration, drug concentration, metabolite concentration, and combinations thereof,
  wherein said sulfide supply, first conduit, patient, and second conduit form a recirculation loop.

14. The apparatus of claim 1, and further comprising a sensor connected to the controller and configured to measure a state of the sulfide-containing perfusion fluid, said state being selected from the group consisting of pH, osmolarity, nutrient concentration, drug concentration, metabolite, and combinations thereof.

15. The apparatus of claim 5, and further comprising one or more sensors configured to measure a state of an effluent of the perfusion fluid, said state being selected from the group consisting of: pH, temperature, pressure, sulfide concentration, osmolarity, nutrient concentration, drug concentration, metabolite concentration, and combinations thereof.

* * * * *